(12) United States Patent
Wahl et al.

(10) Patent No.: US 11,259,698 B2
(45) Date of Patent: Mar. 1, 2022

(54) APPARATUS AND METHOD FOR CAPTURING A VISUAL FIELD OF A PERSON HAVING A SCOTOMA

(71) Applicant: Carl Zeiss Vision International GmbH, Aalen (DE)

(72) Inventors: Siegfried Wahl, Donzdorf (DE); Katharina Rifai, Tübingen (DE); Maria Jose Barraza-Bernal, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 413 days.

(21) Appl. No.: 16/354,424

(22) Filed: Mar. 15, 2019

(65) Prior Publication Data
US 2019/0282082 A1  Sep. 19, 2019

(30) Foreign Application Priority Data
Mar. 16, 2018 (DE) .......................... 102018106125.0

(51) Int. Cl.
*A61B 3/024* (2006.01)
*A61B 3/00* (2006.01)
(Continued)

(52) U.S. Cl.
CPC ............ *A61B 3/024* (2013.01); *A61B 3/0025* (2013.01); *A61B 3/0041* (2013.01);
(Continued)

(58) Field of Classification Search
CPC ..... A61B 3/024; A61B 3/0025; A61B 3/0041; A61B 3/0091; A61B 3/113; A61B 3/112;
(Continued)

(56) References Cited

U.S. PATENT DOCUMENTS

| 6,736,511 B2* | 5/2004 | Plummer ............... A61B 3/024 351/224 |
| 9,861,274 B2 | 1/2018 | Aguilar et al. |

(Continued)

FOREIGN PATENT DOCUMENTS

| CN | 1827035 A | 9/2006 |
| CN | 105637570 A | 6/2016 |

(Continued)

OTHER PUBLICATIONS

European Search Report issued in EP 19156430, which is a counterpart hereof, dated Aug. 13, 2019.

*Primary Examiner* — Travis S Fissel
(74) *Attorney, Agent, or Firm* — Thrive IP®; Georg M. Hasselman (57) ABSTRACT

A method and an apparatus for capturing a visual field of a person having a scotoma, in particular a central scotoma, are disclosed. The method includes continuously capturing the eye alignment of the person with a capturing unit, sampling the visual field of the person point-by-point to determine points suitable and not suitable for sight in the visual field of the person, finding the scotoma as a region with a multiplicity of points not suitable for sight, calculating an outer boundary line of the scotoma, calculating an outer enveloping curve, which surrounds the outer boundary line of the (Continued)

scotoma at a predetermined distance, and displaying the outer enveloping curve on a display unit. The enveloping curve is perceivable by the person on the display unit as a frame of the scotoma.

19 Claims, 5 Drawing Sheets

(51) Int. Cl.
*A61B 3/113* (2006.01)
*A61B 3/12* (2006.01)
*A61B 5/11* (2006.01)
*A61H 5/00* (2006.01)

(52) U.S. Cl.
CPC ............ *A61B 3/0091* (2013.01); *A61B 3/113* (2013.01); *A61B 3/12* (2013.01); *A61B 5/1114* (2013.01); *A61H 5/00* (2013.01); *A61H 2201/50* (2013.01); *A61H 2201/5064* (2013.01); *A61H 2201/5097* (2013.01)

(58) Field of Classification Search
CPC .. A61B 3/13; A61B 3/14; A61B 3/028; A61B 3/032; A61B 5/1114; A61H 5/00; A61H 2201/5064; A61H 2201/5097; A61H 2201/50
USPC ......... 351/205, 206, 208–211, 224, 226, 246
See application file for complete search history.

(56) References Cited

U.S. PATENT DOCUMENTS

| 10,687,700 | B2 | 6/2020 | Kawahara et al. |
| 10,765,314 | B2* | 9/2020 | Yam .................... A63B 24/0003 |
| 2004/0057013 | A1* | 3/2004 | Cappo .................... A61B 3/024 351/224 |
| 2004/0125341 | A1* | 7/2004 | Fink ........................ A61B 3/022 351/211 |
| 2015/0250583 | A1* | 9/2015 | Rosen .................... A61F 2/1645 623/6.23 |
| 2016/0198941 | A1* | 7/2016 | Aguilar .................... G06T 7/50 351/205 |
| 2018/0104106 | A1 | 4/2018 | Lee et al. |

FOREIGN PATENT DOCUMENTS

| CN | 106037625 A | 10/2016 |
| CN | 106037626 A | 10/2016 |
| CN | 107847122 A | 3/2018 |
| CN | 107847354 A | 3/2018 |
| EP | 3111828 A1 | 1/2017 |
| JP | 2006280665 A | 10/2006 |
| WO | 2016/182514 A1 | 11/2016 |
| WO | 2017001335 A1 | 1/2017 |

* cited by examiner

APPARATUS AND METHOD FOR CAPTURING A VISUAL FIELD OF A PERSON HAVING A SCOTOMA

CROSS REFERENCE TO RELATED APPLICATIONS

This application claims priority to German patent application DE 10 2018 106 125.0 filed on Mar. 6, 2018, which is hereby incorporated by reference in its entirety.

TECHNICAL FIELD

The disclosure relates to an apparatus and a method for capturing a visual field of a person having a scotoma. A scotoma is a portion of the visual field whose sensitivity is reduced or has been completely lost—usually for pathological reasons. Scotomata may occur as a result of a disorder of the retina, the optic tract, and/or the visual center.

The disclosure relates to a central scotoma, in particular. A central scotoma relates to complete or partial loss of the central visual field, i.e., a loss of sensitivity in the region of the macula, in particular in the region of the fovea.

BACKGROUND

Normally, the loss of the central visual field is compensated by using remaining healthy regions of the retina. Such a region is referred to as a preferred retinal locus (PRL) for fixation.

It is known that patients do not always form preferred retinal loci for fixation in regions that are optimal for a specific visual task. By way of example, patients often form a preferred retinal locus for fixation on the left side of the scotoma. However, this region is not advantageous for reading text from left to right.

Furthermore, the shape of the scotoma also plays an important role for managing specific visual tasks. The shape of scotomata differs between different patients and, moreover, may change over time. Therefore, it is not possible to determine a generally valid, optimal preferred retinal locus for fixation, which would be applicable to every patient. Instead, the optimal preferred retinal locus for fixation should be determined specifically for each patient on the basis of the shape of the scotoma and the specific visual task.

The publication EP 3 111 828 A1, the content of which is incorporated herewith by reference, has disclosed that the position of the preferred retinal locus for fixation can be influenced by various training strategies. As a result, the preferred retinal locus for fixation can be displaced from an inefficient locus to an efficient locus.

Various methods are known for measuring the visual field of a patient, for example perimetry (Goldmann perimetry, microperimetry) or campimetry. However, these methods do not supply sufficient information about the shape of a scotomata. Therefore, these methods do not facilitate a determination of an optimal preferred retinal locus for fixation as a function of the shape of the scotoma.

Furthermore, imaging methods, such as scanning laser ophthalmoscopy (SLO), optical coherence tomography (OCT), or fundus photography are used for imaging the retina. These methods render it possible to determine damaged regions of the retina and the shape thereof in an objective manner. However, it is not possible to determine the visual field that is subjectively perceived by the patient.

The international patent application WO 2017/001335 A1 relates to an apparatus and a computer program for training a preferred retinal locus for fixation.

The Japanese patent application JP 2006 280 665 A relates to a perimeter.

SUMMARY

It is an object of the disclosure to overcome the disadvantages of the related art. In particular, the intention is to provide an apparatus and a method that can be used to capture scotomata in the visual field of a patient in particularly precise fashion and ensure that the patient is informed particularly precisely about the scotoma. This should improve the effectiveness of training the preferred retinal locus of fixation.

According to the disclosure, this object is achieved by the exemplary embodiments of the method and apparatus as disclosed herein.

The method according to the disclosure for capturing a visual field of a person having a scotoma, in particular a central scotoma, comprises the following steps:

continuously capturing the eye alignment of the person by means of a capturing unit, sampling the visual field of the person point by point to determine points suitable and not suitable for sight in the visual field of the person, finding the scotoma as a region with a multiplicity of points not suitable for sight, calculating an outer boundary line of the scotoma, calculating an outer enveloping curve, which surrounds the outer boundary line of the scotoma at a predetermined distance, and displaying the outer enveloping curve on a display unit with the continuously captured eye alignment being taken into account, in such a way that the outer enveloping curve is perceivable as a frame of the scotoma by the person in the case of any alignment of the eye of the person onto the display unit.

Thus, according to the disclosure, the person can perceive the outer enveloping curve with regions of the intact retina that immediately surround the scotoma. Thus, the outer enveloping curve frames the region of the scotoma in the perception of the person. According to an advantageous embodiment of the disclosure, the outer enveloping curve is displayed on the display unit taking account of the continuously captured eye alignment in such a way that the outer enveloping curve is perceivable by the person by way of points in the visual field suitable for sight, which were determined previously according to the method, and which lie in the immediate vicinity of the points unsuitable for sight, which form the scotoma.

In particular, the position, size, and/or shape of the scotoma of the person can be determined using the method according to the disclosure.

The method according to the disclosure is applicable both in the case of monocular vision (with one eye) and in the case of binocular vision (with both eyes simultaneously). By way of example, the second eye can be covered for an application of the method with monocular vision. In terms of its phrasing, the subsequent description relates to the case of monocular vision. However, it is self-evident that the terms "an eye" or "the eye" can also be read with the meaning of "both eyes" or "both eyes simultaneously."

Within the scope of the method according to the disclosure, the visual field of the person can be captured in its entirety or else only in part. Typically, the visual field is captured in the region of the scotoma and in regions immediately surrounding the scotoma (i.e., the immediate neighborhood of the scotoma).

The point-by-point sampling of the visual field of the person is typically implemented with the display unit. Typically, the display unit is arranged with respect to the position of the eye of the person with a defined spatial relationship.

Within the meaning of the disclosure, the phrase "point-by-point sampling" should not be understood to be restricted to the literal sense. Typically, the visual field is divided into individual sectors of a polar coordinate system for the purpose of point-by-point sampling. In particular, the individual sectors are sampled in succession. Therefore, the phrase "point-by-point sampling" may also be used interchangeably with the phrase "sector-by-sector sampling" or "sequential sampling." Further, the term "sampling" can be used interchangeably with the terms "detecting" or "measuring." Within the meaning of the disclosure, the term "sampling" should not be interpreted to mean a continuous sweeping over a line or an area; instead the term relates to the detection of discrete measurement points or loci, typically discrete sectors. Thus, each sector typically comprises at least one respective measurement point.

The level of resolution of the point-by-point sampling can be adjusted. Typically, the resolution is determined by the size of the sectors. For sectors with a distance from the fovea with an angular diameter of less than 2 degrees, the resolution can be an angular diameter of 0.05° to 0.15°, typically an angular diameter of 0.08° to 0.12°, particularly typically an angular diameter of 0.1°. For peripheral sectors with a distance from the fovea with an angular diameter of more than 20 degrees, the resolution can be an angular diameter of 1° to 3°, typically an angular diameter of 1.5° to 2.5°, particularly typically an angular diameter of 2°.

For the purposes of determining the outer boundary line, the edge sectors forming an edge of the scotoma are typically determined first, i.e., sectors that themselves are not subjectively visible P to the person and that are adjacent to sectors that are and are not subjectively visible P to the person. By way of example, the outer boundary line can be determined from the center points of these edge sectors, by determining respectively adjacent edge sectors, and by connecting the center points of respectively adjacent edge sectors in piecewise fashion using straight lines. Alternatively, the outer boundary line may also be determined, for example, by calculating a fitted curve in relation to the center points of the edge sectors. As yet another alternative thereto, the outer boundary line can be determined as the line immediately surrounding the edge sectors on the outer side of the scotoma. Typically, the aforementioned determination, connection, and/or calculation steps are carried out by an algorithm.

The predetermined distance typically is an angular diameter of between 0.3° and 0.8°, more typically an angular diameter of between 0.4° and 0.6°. A predetermined distance with an angular diameter of 0.5° was found to be particularly advantageous. Two criteria should typically be taken into account when setting the predetermined distance. Firstly, the outer enveloping curve should lie as close as possible to the scotoma; secondly, the outer enveloping curve should lie in the region of a retina that is completely intact.

By way of example, the outer enveloping curve can be produced by binary dilation at a predetermined distance from the outer boundary line. Here, a circle, for example, can be used as structuring element.

Displaying the outer enveloping curve as a frame of the scotoma provides precise and intuitive feedback for the person in respect of the size and shape of the scotoma.

According to an exemplary embodiment of the disclosure, the method comprises the further step of:

determining a position of a preferred retinal locus for fixation.

To this end, the person should use one eye (or both eyes) to fixate on a fixation point displayed on the display unit. In the case of a person having a central scotoma, the fixation is not implemented by means of the fovea—as would be the case for a healthy person, for instance—but by means of the preferred retinal locus for fixation as a fovea replacement. The position of the preferred retinal locus for fixation is typically determined by evaluating the eye alignment during fixation on the fixation point. Typically, the mainly prevalent eye alignment—while the person should fixate on the fixation point—is assumed to be the position of the preferred retinal locus for fixation. A plurality of preferred retinal loci for fixation are formed in some persons. By way of example, the plurality of preferred retinal loci for fixation can be embodied for specific visual tasks in each case. Accordingly, provision can be made for the presence of a plurality of preferred retinal loci for fixation to be captured and for their respective position to be determined.

According to a further exemplary embodiment of the disclosure, provision is made for the point-by-point sampling of the visual field of the person to be implemented while the person should fixate on a fixation point, permanently displayed on the display unit, with the preferred retinal locus for fixation. Typically, point-by-point sampling is implemented by a sampling point that is intermittently displayed on the display unit and individual points of the visual field are successively captured in polar coordinates with distance $\rho$ and angle $\theta$ in respect of the preferred retinal locus for fixation within the scope of point-by-point sampling by the sampling point.

This configuration is easy to implement, means no additional outlay in terms of apparatus, and achieves precise results.

Within the meaning of the disclosure, the terms "fixation point" and "sampling point" should by no means be understood as being restricted to only a single point.

The sampling point can be a sampling object with any shape that is displayable on the display unit. The sampling point can be an abstract geometric object, for example a point, a circle, an ellipse, a rectangle, a square, or any other polygon. This object may be filled or else only have an outer contour. By way of example, the sampling point can be a circular disc or a circular ring. The sampling point may be unicolored, in particular black or white, or multicolored. In particular, the sampling point can be a specific object, for example a star, a football, a flower, a cat, or a human. The specific object can be drawn or sketched. However, the specific object may also be photorealistic. The sampling point may be animated, i.e., carry out a movement, typically a movement in one place. By way of example, the sampling point may carry out a rotational movement or a pulsating movement.

The fixation point can be a fixation object with any shape that is displayable on the display unit. The fixation point can be an abstract geometric object, for example a point, a circle, an ellipse, a rectangle, a square, or any other polygon. This object may be filled or else only have an outer contour. By way of example, the fixation point can be a cross. The fixation point may be unicolored, in particular black or white, or multicolored. In particular, the fixation point can be a specific object, for example a star, a football, a flower, a cat, or a human. The specific object can be drawn or sketched. However, the specific object may also be photo-realistic. The fixation point may be animated, i.e., carry out a movement, typically a movement in one place. By way of example, the fixation point may carry out a rotational movement or a pulsating movement.

Typically, the sampling point differs from the fixation point in terms of shape, size, and/or color. Also typically, the sampling point and the fixation point are different objects.

The sampling point is typically displayed for a predetermined period of time at a predetermined location on the display unit and disappears after this predetermined period of time has expired. Subsequently, the sampling point is respectively displayed for the predetermined period of time at a respective different predetermined location on the display unit and disappears again in each case after the predetermined period of time has expired.

As already described above, the visual field is typically divided into individual sectors of a polar coordinate system for the purposes of point-by-point sampling. Typically, the sampling point at a given time is assigned to a predetermined sector and displayed on the display unit for a predetermined period of time in such a way that the visual field of the person in a region corresponding to this sector is impinged upon by the sampling point when fixating the eye or the eyes on the fixation point. After the predetermined period of time has expired, the sampling point disappears from the display unit. At a subsequent time, the sampling point is assigned to another sector and displayed on the display unit for the predetermined period of time in such a way that the visual field of the person in a region corresponding to this other sector is impinged upon by the sampling point when fixating the eye or the eyes on the fixation point. In this way, the sampling point successively passes through the individual sectors. Provision can be made for the sampling point to reach all sectors of the visual field or only certain sectors, for example only the sectors in the central region, particularly typically only sectors with a distance with an angular diameter of no more than 5° from the preferred retinal locus for fixation. Typically, the size of the sampling point is guided by the size of the respective sector. Provided there is an assignment to a certain sector, the sampling point may also be larger than the sector.

The size of the sampling point may vary, particularly as a function of its position in the visual field. By way of example, sectors in the peripheral region of the visual field are larger than sectors in the central region of the visual field in the case where the visual field is represented by polar coordinates. Accordingly, the sampling point for a position in the peripheral region of the visual field may be greater than a sampling point for a position in the central region of the visual field.

The sampling point and/or the fixation point may be embedded in a pattern or be part of the pattern. By way of example, the pattern can be a radial frequency pattern. The sampling point and/or the fixation point may be embedded in a drawn or photorealistic image or be part of the image. The image can be a Waldo image, for example. The image can be a still or an animated image. The sampling point and/or the fixation point can be embedded in a film sequence or may appear and/or disappear in the film sequence. Furthermore, the sampling point can be embedded at a different spatial depth into an image (still, animated image, or film sequence). Furthermore, the sampling point and/or the fixation point can be embedded in a virtual reality or augmented reality scenario or can be a part thereof.

In the case of a plurality of preferred retinal loci for fixation, the point-by-point sampling can be carried out individually in each case for the individual preferred retinal loci for fixation. As an alternative thereto, the positional relationship between the individual preferred retinal loci for fixation (i.e., the distance $\rho$ and the respective angle $\theta$ thereof) can be determined and common sampling for the plurality of preferred retinal loci for fixation can be carried out on the basis thereof.

By way of an additional signal, the person can be notified about the display of the sampling point on the display unit. The additional signal can be an audio signal and/or a haptic signal. The additional signal can indicate the display of the sampling point on the display unit during precisely the entire display duration of the sampling point and can end only once the sampling point goes out.

According to a further exemplary embodiment of the disclosure, provision is made for the person to be questioned in relation to the subjective visibility P of each point ($\rho$, $\theta$) to the person. Here, a 3×n matrix with entries ($\rho$, $\theta$, P) is formed for n points ($\rho$, $\theta$) captured in this way and/or a visual field map is formed as a graphical representation of the n captured points ($\rho$, $\theta$).

Querying the subjective visibility P can be implemented by virtue of the person receiving one or more buttons for operating purposes and the person communicating whether the sampling point was visible or whether the sampling point was not visible by pressing an appropriate button or by not pressing a button. Furthermore, querying of the subjective visibility P can be implemented by way of voice recognition. Here, the person should say "yes," for example, if the sampling point was visible, and the person should be silent if the sampling point was not visible. Furthermore, the person can be instructed to signal subjective visibility P by blinking, typically by blinking twice. Accordingly, the subjective visibility P can be queried by detecting the movement of the eyelids.

As an alternative or in addition thereto, the subjective visibility P can also be determined on the basis of a reaction of the pupil of the eye.

By way of example, the subjective visibility P can adopt a value of 1 for the case that the sampling point was visible and can adopt a value of 0 if the sampling point could not be seen.

The different values of P can be represented in different colors or using different symbols on the visual field map.

The shape and size of a scotoma can be determined particularly quickly and effectively with the aid of the visual field map.

Interpolation methods and machine learning can be used to determine the shape and size of the scotoma.

The outer boundary line of the scotoma calculated according to the disclosure can be verified by testing the person. During this testing, the outer enveloping curve is displayed, according to the disclosure, to the person as a frame of the scotoma on the display unit.

By checking discrete scotoma regions, it is possible to undertake relatively fine adjustments of the outer boundary line and/or the outer enveloping curve.

According to a further exemplary embodiment of the disclosure, provision is made for a fixation stability to be determined from the continuously captured eye alignment as a measure for the quality of the fixation by the preferred retinal locus for fixation on the fixation point displayed on the display unit.

Here, a limit for the fixation stability may be predetermined. The method can be configured in such a way that the subjective visibility P to a sampling point is discarded should the fixation stability ascertained during the display of this sampling point drops below this limit.

According to a further exemplary embodiment of the disclosure, provision is made for a correction of the polar coordinates of a point (ρ, θ) in the visual field to be implemented by the continuously captured eye alignment should the fixation point at the moment of sampling by the sampling point not be fixated by the preferred retinal locus for fixation.

By evaluating the continuously captured eye alignment, it is possible to ascertain the positional relationship between the actual locus for fixation while the sampling point is displayed and the preferred retinal locus for fixation. The correction can be carried out on the basis of this positional relationship.

The correction can be carried out depending on the fixation stability. By way of example, a further limit for the fixation stability can be predetermined. The method can be configured in such a way that the correction is carried out should the fixation stability ascertained during the display of the sampling point drops below this further limit.

The point-by-point sampling of the visual field with the aforementioned correction of the polar coordinates (ρ, θ) of the sampling point by means of the continuously captured eye alignment leads to particularly reliable results.

According to a further exemplary embodiment of the disclosure, provision is made for an image of the fundus of the eye of the person to be additionally recorded. Here, the position of the fovea is determined on the basis of the image. The image and/or the position of the fovea are stored.

Different imaging methods can be used for recording the image of the fundus, for example scanning laser ophthalmoscopy (SLO), optical coherence tomography (OCT), or fundus photography. In particular, the positional relationship between the fovea and the preferred retinal locus for fixation can be ascertained on the basis of the image of the fundus and the eye alignment when fixating on a fixation point by means of the preferred retinal locus for fixation.

According to a further exemplary embodiment of the disclosure, provision is made for an optimal region for a specific visual task to be determined from the points suitable for sight in the visual field of the person as a replacement for the preferred retinal locus for fixation.

The optimal region for a specific visual task is referred to below as optimal preferred retinal locus for fixation in this case. The optimal preferred retinal locus for fixation is a locus of replacement for the preferred retinal locus for fixation that is particularly efficient for a specific visual task.

By way of example, the optimal preferred retinal locus for fixation can be determined as a function of the shape and size of the scotoma, in particular on the profile of the outer boundary line of the scotoma, and/or as a function of the previously determined points unsuitable for sight in the visual field of the person.

According to a further exemplary embodiment of the disclosure, provision is made for the continuously captured eye alignment, the points suitable for sight in the visual field of the person, the points unsuitable for sight in the visual field of the person, the outer boundary line of the scotoma, the outer enveloping curve, the position of the preferred retinal locus for fixation, the position of the fovea and/or the optimal region for a specific visual task to be stored with a time entry of the respective determination for the eye or the eyes of the person as current data of the person. Typically by means of artificial intelligence, statements in relation to the further development of the scotoma of the person, the position of the preferred retinal locus for fixation of the person, and/or the optimal region of the person for a specific visual task are produced from the current data of the person, from earlier correspondingly determined data of the person, and/or from correspondingly determined data of other persons.

If a plurality of preferred retinal loci for fixation are present, the positions of each of the preferred retinal loci for fixation are stored. In this case, statements can be produced for the respective positions of the plurality of preferred retinal loci for fixation of the person.

The exemplary embodiment of the disclosure allows, in particular, the subjective measurement of the size and shape of the scotoma of a certain person as a function of time.

Furthermore, specific measures for the person can be determined from the current data of the person, from earlier correspondingly determined data of the person, and/or from correspondingly determined data of other persons. By way of example, a minimum font size that is legible to the person, a training plan, and/or the time of the next examination can be determined.

The exemplary embodiment of the disclosure allows more detailed predictions or prognoses about the development of the scotoma and the prospects of success of the training.

According to a further exemplary embodiment of the disclosure, provision is made for a training of the preferred retinal locus for fixation of the person with the display unit to be carried out in combination with the display of the outer enveloping curve on the display unit.

Training the preferred retinal locus for fixation is carried out with the goal of displacing the position of the preferred retinal locus for fixation into the optimal region for a specific visual task. According to the disclosure, the outer enveloping curve is displayed on the display unit with the continuously captured eye alignment being taken into account, in such a way that the outer enveloping curve is perceivable as a frame of the scotoma by the person in the case of any alignment of the eye of the person onto the display unit. Typically, the outer enveloping curve is displayed continuously during the training on the display unit. The training can be carried out in a particularly preferred fashion by virtue of a scenario from virtual reality or augmented reality additionally being displayed on the display unit. It was found that the training for displacing the preferred retinal locus for fixation to the optimal preferred retinal locus for fixation for the specific visual task is particularly effective when combining a scenario from virtual reality or augmented reality with the continuous display of the outer enveloping curve as a frame of the scotoma.

Typically, the training for specific regions of the visual field may also be implemented for persons without a scotoma. Here, a specific gaze behavior can be trained, for example the gaze behavior when using varifocal lenses.

The apparatus according to the disclosure for capturing a visual field of a person having a scotoma, in particular a central scotoma, comprises a capturing unit for continuously capturing the eye alignment of the person, a display unit for displaying visual information, wherein the display unit is arranged with respect to the position of the eye of the person in a defined and/or determinable spatial relationship, and a control unit for carrying out the method according to the disclosure and/or any of the above-described embodiments thereof.

The point-by-point sampling of the visual field of the person is typically performed with the display unit. The spatial relationship between the display unit and the position of the eye of the person can be fixedly predetermined.

Alternatively, a movement of the position of the eye or of the head of the person relative to the display unit can be allowed and can be determinable by means for determining the position of the eyes or the head.

Typically, the capturing unit is an appliance for capturing the gaze, in particular a so-called eye tracker. The capturing unit typically comprises a camera that is alignable on the eye or both eyes of the person, for continuously recording images of the eye or the eyes. Additionally, the capturing unit may comprise an evaluation unit for evaluating the images and for continuously calculating the eye alignment of the person. Alternatively, provision can be made for images recorded by the camera to be continuously transmitted to the control unit and for the control unit to continuously calculate the eye alignment of the person. Furthermore, the capturing unit may comprise means for determining the position of the eyes or the head. In this case, the capturing unit determines the position of the eyes or the position of the head of the person, in addition to the eye alignment.

The apparatus according to the disclosure may additionally include a feedback unit for capturing the subjective visibility P of a point $(\rho, \theta)$ to the person. The feedback unit can be an actuation unit with one or more buttons, which should be actuated by the person for communicating the subjective visibility P of the point $(\rho, \theta)$. Furthermore, the feedback unit can be a voice recognition unit for capturing and processing a spoken response by the person. The feedback unit can also be configured as an eyelid detection unit for detecting the movement of the eyelids, with the person being instructed to signal the subjective visibility P by blinking, typically by blinking twice. As an alternative or in addition thereto, the feedback unit can also comprise a pupil reaction detection unit for detecting a reaction of the pupil of the eye and for determining the subjective visibility P.

The apparatus and/or the control unit according to the disclosure may additionally comprise a memory unit for storing the continuously captured eye alignment, the points suitable for sight in the visual field, the points unsuitable for sight in the visual field, the outer boundary line of the scotoma, the outer enveloping curve, the position of the preferred retinal locus for fixation, the position of the fovea and/or of the optimal region for a specific visual task, together with a time entry of the respective determination and with an assignment to the respective person. Thus, in particular, current data of the person, earlier correspondingly determined data of the person, and/or correspondingly determined data of other persons may be stored in the memory unit.

The apparatus according to the disclosure and/or the control unit may additionally comprise a prediction unit for producing statements, typically by means of artificial intelligence, about the further development of the scotoma of the person, about the position of the preferred retinal locus for fixation of the person and/or about the optimal region of the person for a specific visual task from the current data the person, from earlier correspondingly determined data of the person and/or from correspondingly determined data of other persons.

According to an exemplary embodiment of the disclosure, provision is made for the display unit to be a screen, in particular a spherically formed screen, and for the apparatus to furthermore comprise means for placing the head of the person in a position that is defined relative to the screen and/or means for determining the position of the head relative to the screen.

Here, provision can be made of a chin rest, in particular, as a means for placing the head of the person in a position that is defined relative to the screen.

The means for determining the position of the head relative to the screen can be provided by the capturing unit. In this case, the head position and/or the eye position of the person, in addition to the eye alignment, are also calculated continuously by the evaluation unit or by the control unit on the basis of the images continuously recorded by the camera.

As an alternative thereto, the means for determining the position of the head relative to the screen can be provided by a separate position determining unit. The position determining unit can be a further eye tracker. The position determining unit typically comprises a camera that is alignable on the head or the eye or the eyes of the person, for continuously recording images of the head or the eye or the eyes. The position determining unit or the control unit is used to continuously calculate the head position and/or the eye position of the person from the images continuously recorded by the camera.

The means for determining the position of the head relative to the screen allow free movement of the person within a defined spatial region. A person sitting on a seat may move freely, for example, in this exemplary embodiment.

According to an alternative exemplary embodiment of the disclosure, provision is made for the display unit and the capturing unit to be provided in a head unit that is fastened to the head of the person.

The unit fastened to the head is referred to below as a head-mounted display, as is generally conventional. The control unit can be integrated into the head-mounted display or can be embodied as an independent component on the body of the person or can be arranged in stationary fashion, i.e., independently of the movement of the person. A data link can be provided between the control unit and the head-mounted display. The data link can have a wired embodiment or an embodiment as a radio connection (WLAN, Bluetooth, etc.). Furthermore, the head-mounted display may comprise one and more position sensors, in particular a magnetometer, an acceleration sensor, and/or a gyroscope. A smartphone worn on the body of the person, for example in a pants pocket, may act as a control unit. Furthermore, the control unit, the display unit, and/or the capturing unit can be realized by a smartphone used as a head-mounted smartphone with a specific holder.

This embodiment of the display unit and the capturing unit as a constituent part of a head-mounted display is particularly typical for displaying virtual reality or augmented reality. Here, it was found that the combination of a virtual reality or augmented reality scenario with the display of the outer enveloping curve as a frame of the scotoma on the head-mounted display makes the training of the preferred retinal locus for fixation particularly effective.

The apparatus according to the disclosure or the advantageous configurations thereof described above may facilitate further types of training, for example the training for specific regions of the visual field in the case of persons without a scotoma. Here, a specific gaze behavior can be trained, for example the gaze behavior when using varifocal lenses.

The method according to the disclosure and/or any of the above-described exemplary embodiments thereof may be computer-implemented. According to the disclosure, provision is made, in particular, of a computer program with program code that is executable on a processor for carrying out the method steps of the method according to the disclosure and/or of any of the above-described embodiments thereof. In particular, the computer program carries out the method steps of the method according to the disclosure by virtue of running through an algorithm.

To this end, the computer program is loaded onto a computer or carried out on a computer. The control unit can be configured as a computer or can comprise a computer. Alternatively, the computer can comprise the control unit.

According to the disclosure, provision is furthermore made of a non-transitory computer storage medium with a computer program according to the disclosure stored thereon.

Typically, the disclosure facilitates a direct and precise determination of the size, the shape, and the development of a scotoma, in particular a central scotoma. The use of a virtual reality or augmented reality scenario contributes particularly to the motivation of the patient. Such a scenario engrosses the patient and prevents the patient dulling as a result of boredom. The combination of a virtual reality or augmented reality scenario with the display of the outer enveloping curve as a frame of the scotoma, in particular on a head-mounted display as a display unit, is particularly advantageous. Advantageously, an optimum preferred retinal locus for fixation is determined as a function of the shape of the scotoma and as a function of the specific visual task. What was found is that, in this case, the training for displacing the preferred retinal locus for fixation to the optimal preferred retinal locus for fixation for the specific visual task is particularly effective.

BRIEF DESCRIPTION OF THE DRAWINGS

The disclosure will now be described with reference to the drawings wherein.

DESCRIPTION OF EXEMPLARY EMBODIMENTS

Figure 1:
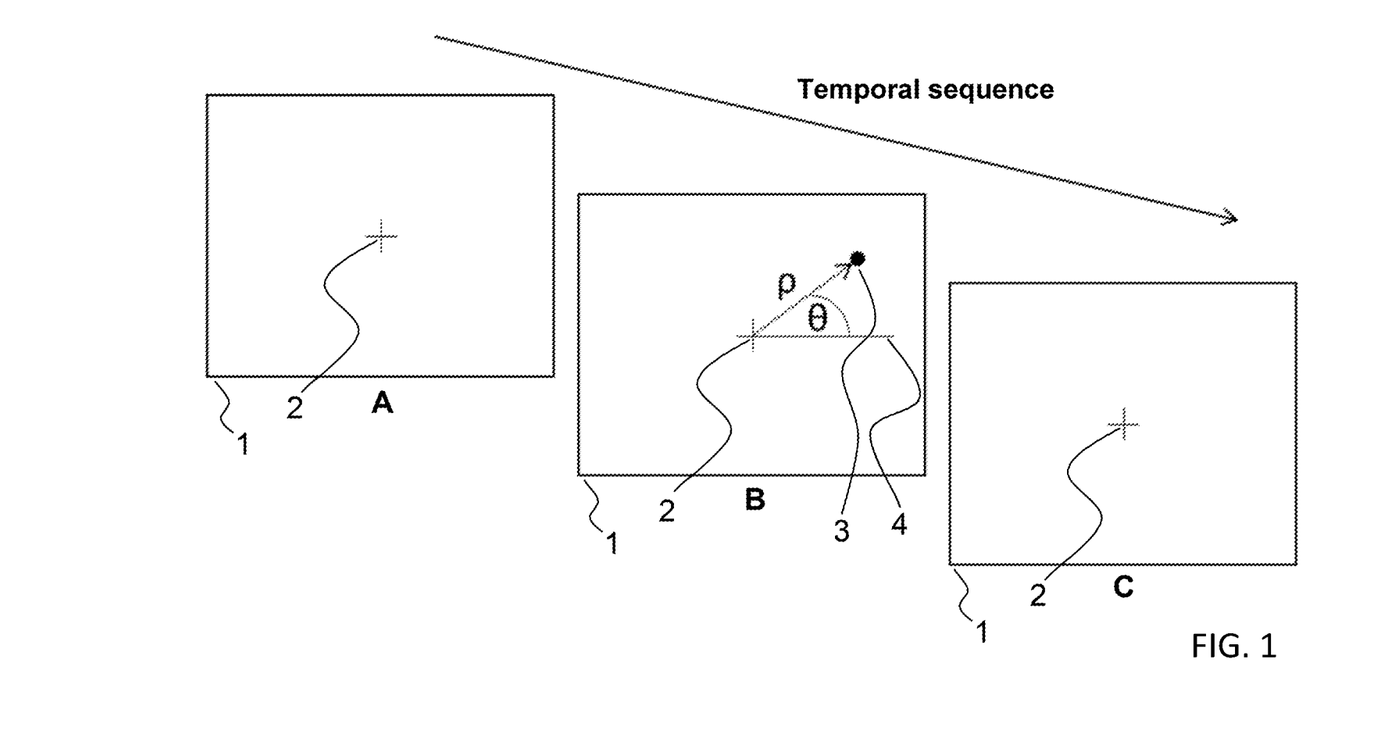
FIG. 1 shows a temporal sequence for point-by-point sampling of the visual field.

FIG. 1 shows a temporal sequence of the point-by-point sampling of the visual field. Here, a display unit 1, in particular a screen, is shown at three different successive times A, B, and C. A person is instructed to fixate on the fixation point 2, displayed permanently on the display unit 1, with their left and/or right eye. By way of example, the fixation point 2 is configured as a cross. Additionally, a sampling point 3 appears on the display unit 1 for a predetermined period of time at the time B. By way of example, the sampling point 3 is configured as a circular disc and (its center) has a distance ρ from the fixation point 2 and an angle θ in relation to a line typically extending horizontally through the fixation point 2. Thus, the fixation point 2 defines the origin of a polar coordinate system with the line as polar axis 4. The sampling point 3 is located in this polar coordinate system by the polar coordinates (ρ, θ). In addition to displaying the sampling point 3, the person's attention is drawn to the simultaneous display of the sampling point 3 by means of an acoustic or haptic signal. The person is instructed to communicate with a feedback unit (not shown) whether the sampling point 3 is perceived. By way of example, the feedback unit may comprise a button that should be pressed when the sampling point 3 is perceived. After the predetermined period of time has expired, the sampling point 3 disappears (time C). The acoustic or haptic signal also ends. Typically, pressing of the button that takes place after the sampling point 3 has disappeared is captured by the feedback unit and assigned to the sampling point 3 that has disappeared. After the button being pressed has been captured by the feedback unit and/or after a further period of time has expired, the sampling point 3 appears at another location on the display unit 1, typically, once again, for the predetermined period of time (not shown). The display is once again accompanied by the acoustic or haptic signal. After the predetermined period of time has expired, the sampling point 3 disappeares again (not shown). This sequence is carried out for a total of n different locations on the display unit 1. Thus, the subjective visibility P to the person is captured in each case in this procedure for n pairs of polar coordinates (ρ, θ). P can adopt the values of 1 (sampling point 3 is perceivable by the person) or 0 (sampling point 3 is not perceivable by the person). The captured data are stored specifically for the person in a memory unit with the capture time. The captured data can be represented as a 3×n matrix with line-by-line or column-by-column entries (ρ, θ, P).

Figure 2:
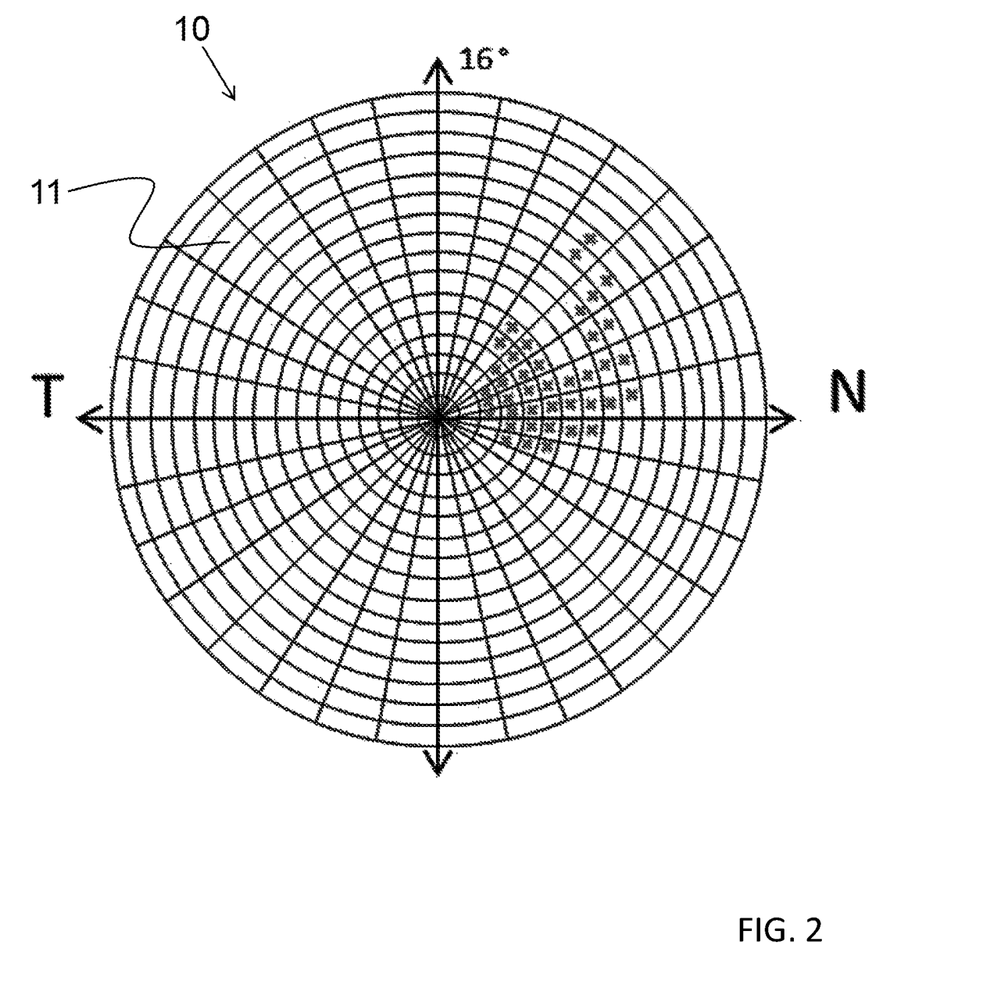
FIG. 2 shows a visual field map as a graphical representation of the subjective visibility P of the n captured points (ρ, θ)

The captured data can be represented more clearly as a visual field map. FIG. 2 shows a visual field map 10 as a graphical representation of the subjective visibility P of the n captured points (ρ, θ). The visual field map 10 is a representation of the visual field in polar coordinates. Here, the visual field is subdivided into polar sectors 11. The point-by-point sampling of the visual field, described in conjunction with FIG. 1, is carried out in such a way that one sampling point 3 is in each case assigned to a polar sector 11 of the visual field map 10. Here, all polar sectors 11 present in the visual field map 10 can be captured by a sampling point 3 in each case. However, a selection of n polar sectors 11 is typically made for capturing the subjective visibility P. Typically, only polar sectors 11 in the central region and/or in regions in which no subjective visibility (P=0) has already been determined for the person in earlier measurements, and regions with subjective visibility (P=1) adjacent thereto are captured. In the example of FIG. 2, all polar sectors 11 in which the sampling point 3 was not perceivable by the person in each case (P=0) are marked by an "x." As an alternative or in addition thereto, these sectors can be illustrated using a certain color, e.g., red. In FIG. 2, T represents temporal; N represents nasal. With 16°, a reference value of the eccentricity is specified. However, the measurement of the visual field may also be implemented beyond 16°.

Figure 3:
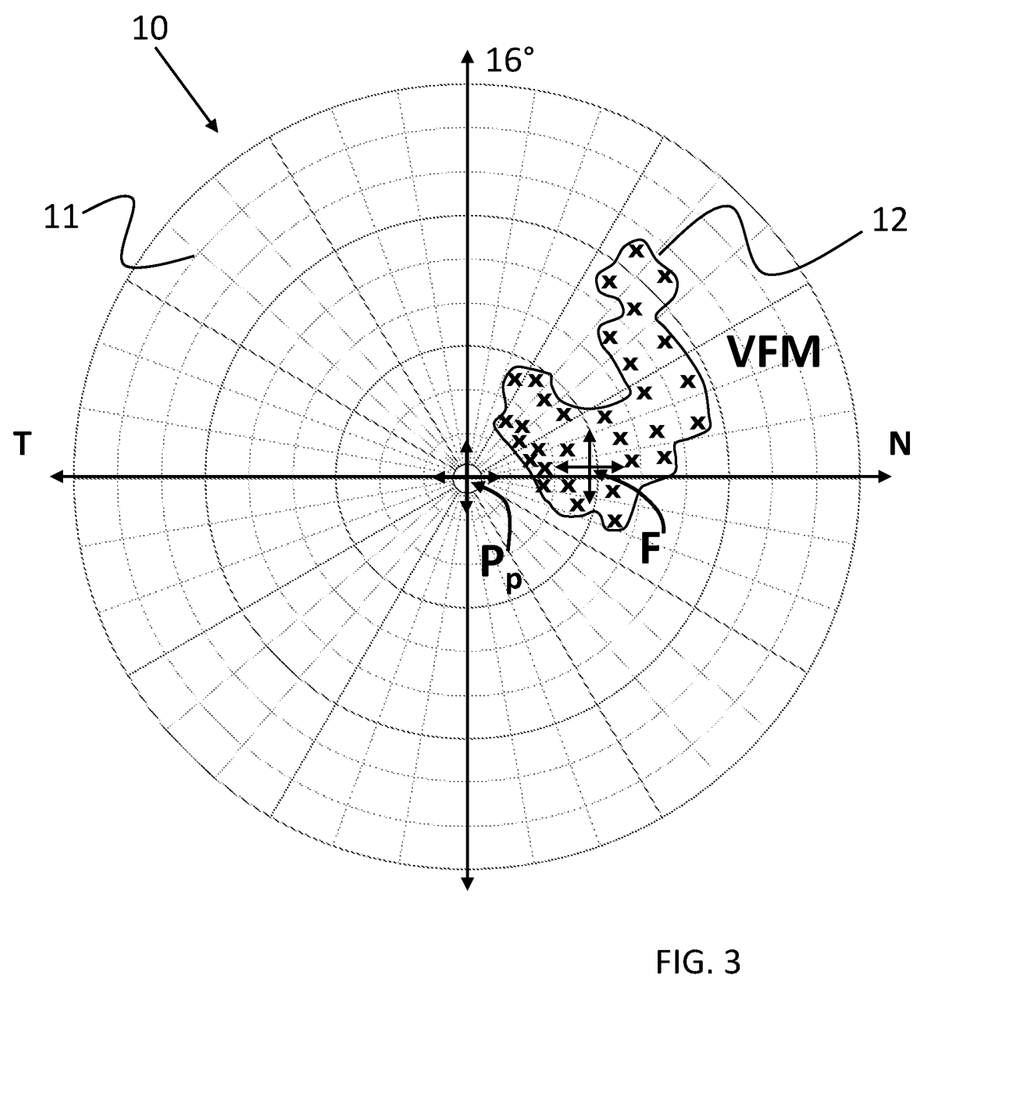
FIG. 3 shows the visual field map (VFM) with the outer boundary line of the scotoma.

FIG. 3 shows the visual field map 10 of FIG. 2 after the control unit found a scotoma in the visual field of the person from the arrangement of the polar sectors 11 with P=0 and after the outer boundary line 12 of the found scotoma was calculated. The outer boundary line 12 is schematically plotted in the shape of straight pieces in FIG. 3. The straight pieces connect the centers of the edge sectors forming an edge of the scotoma. However, the outer boundary line 12 can also be determined as a continuous smooth line. The outer boundary line 12 can be illustrated using a certain color, e.g., green. Additionally, FIG. 3 plots the position of the preferred retinal locus for fixation $P_p$. Since the person fixates the fixation point 2 with their preferred retinal locus for fixation $P_p$, the preferred retinal locus for fixation $P_p$ is the origin of the polar coordinate system. Additionally, a capturing unit can continuously capture the eye alignment Eye(x,y) of the person during the point-by-point sampling described in relation to FIG. 1. The eye alignment Eye(x,y) captured thus can be stored specifically for the person together with the above-described data relating to ρ, θ, and P, in particular with the 3×n matrix, for the capture time. The position of the preferred retinal locus for fixation $P_p$ in relation to the optic axis can be determined in this case by evaluating the eye alignment Eye(x,y) captured by the capturing unit while fixating on the fixation point 2. Additionally, the polar coordinates (ρ, θ) in relation to a sampling point 3 can be corrected in this case should the eye alignment Eye(x,y) during the display of the sampling point 3 not correspond to the preferred retinal locus for fixation $P_p$ of the person. Furthermore, the position of the fovea F is plotted in FIG. 3. The position of the fovea F can be determined by the additional recording of an image from the fundus of the eye of the person. Different imaging methods can be used to this end, for example scanning laser ophthalmoscopy (SLO), optical coherence tomography (OCT), or fundus photography. The positional relationship between the fovea F and the preferred retinal locus for fixation can be ascertained on the basis of the image of the fundus and the eye alignment Eye(x,y) when fixating on the fixation point 2 by means of the preferred retinal locus for fixation $P_p$.

Figure 4:
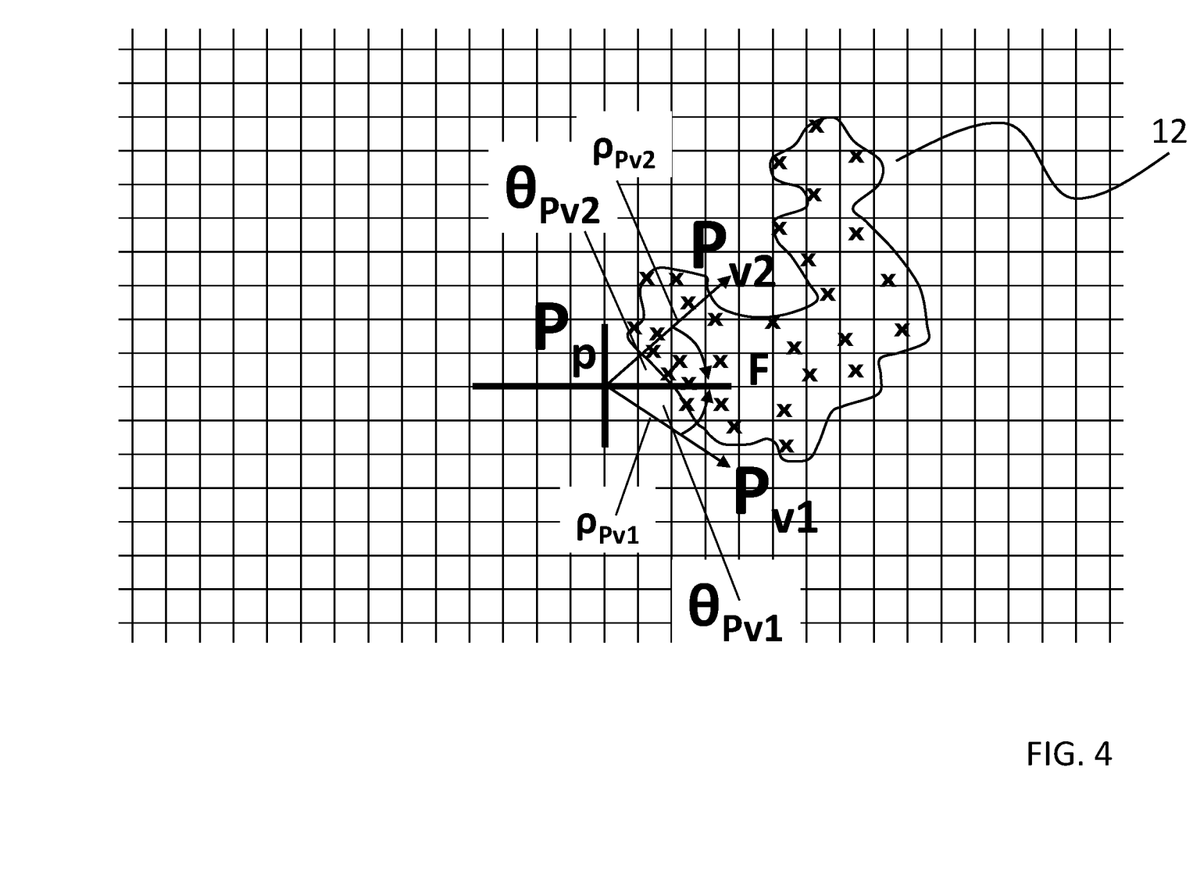
FIG. 4 shows a further representation of the visual field map with two additionally plotted optimal preferred retinal loci for fixation for two different specific visual tasks.

FIG. 4 shows a further representation of the visual field map with two additionally plotted optimal preferred retinal loci for fixation for two different specific visual tasks. A first optimal preferred retinal locus for fixation $P_{v1}$ can be calculated by the control unit for a first specific visual task v1. Accordingly, a second optimal preferred retinal locus for fixation $P_{v2}$ can be calculated by the control unit for a second specific visual task v2. The first optimal preferred retinal locus for fixation $P_{v1}$ and the second optimal preferred retinal locus for fixation $P_{v2}$ are plotted in FIG. 4. By way of example, the first optimal preferred retinal locus for fixation $P_{v1}$ is optimized for a visual task that requires a position of the preferred retinal locus for fixation below the scotoma, in particular for reading a text. By way of example, the second optimal preferred retinal locus for fixation $P_{v2}$ is optimized for a visual task that requires a position of the preferred retinal locus for fixation in the vicinity of the fovea F. Furthermore, the control unit can calculate first translation variables $\rho_{Pv1}$ and $\theta_{Pv1}$ for a translation of the present preferred retinal locus for fixation $P_p$ to the first optimal preferred retinal locus for fixation $P_{v1}$ and second translation variables $\rho_{Pv2}$ and $\theta_{Pv2}$ for a translation of the present preferred retinal locus for fixation $P_p$ to the second optimal preferred retinal locus for fixation $P_{v2}$. The first translation variables ($\rho_{Pv1}$, $\theta_{Pv1}$) and the second translation variables ($\rho_{Pv2}$, $\theta_{Pv2}$) are likewise plotted in FIG. 4.

Figure 5:
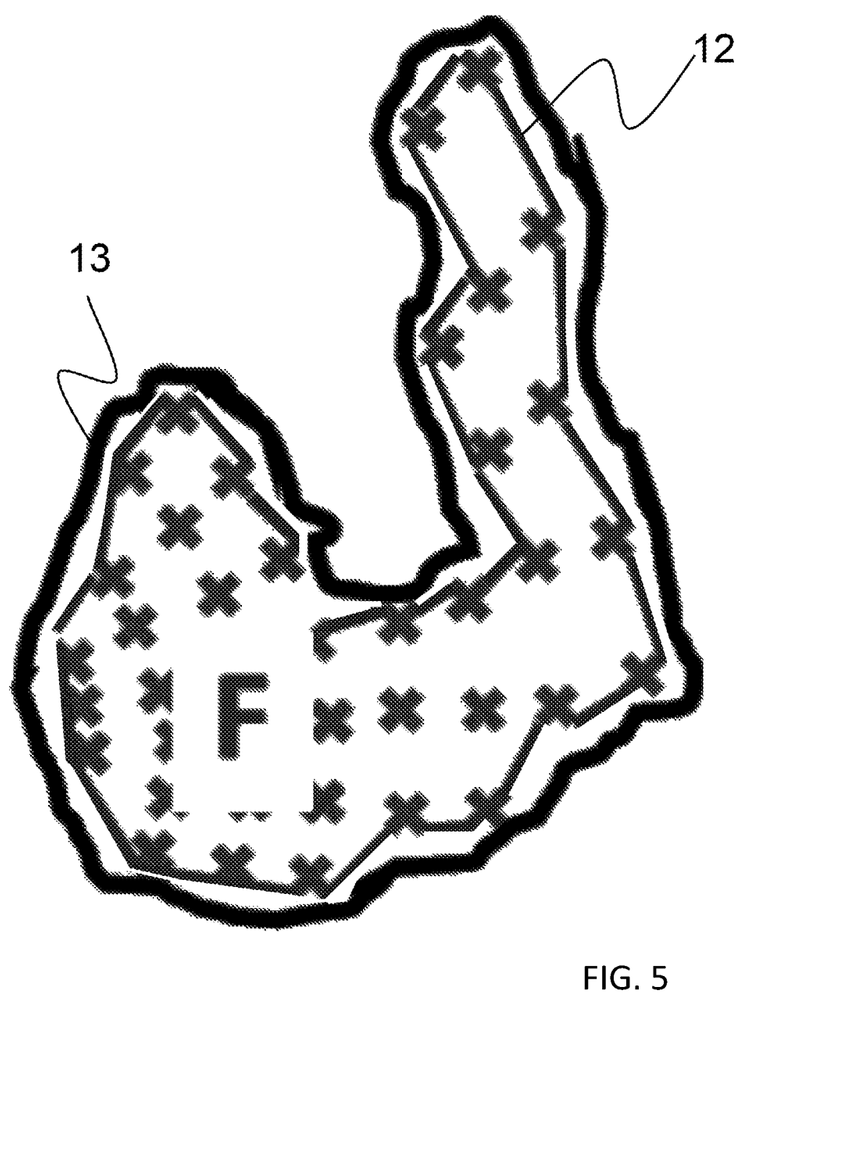
FIG. 5 shows a magnified schematic illustration of the scotoma with an outer boundary line and an outer enveloping curve.

FIG. 5 shows a magnified schematic illustration of the scotoma. The control unit can calculate an outer enveloping curve 13 on the basis of the outer boundary line 12. The outer enveloping curve 13 is calculated in such a way that it surrounds the outer boundary line 12 at a predetermined distance. The predetermined distance typically approximately has an angular diameter of 0.5°.

The outer enveloping curve 13 can be displayed on the display unit 1 with the continuously captured eye alignment Eye(x,y) being taken into account in such a way that the outer enveloping curve 13 is perceivable as a frame of the scotoma by the person in the case of any alignment of the eye onto the display unit 1. As a result, the person can perceive the outer enveloping curve 13 with regions of the intact retina that immediately surround the scotoma. Thus, the outer enveloping curve 13 frames the region of the scotoma in the perception of the person.

Displaying the outer enveloping curve 13 as a frame of the scotoma provides precise and intuitive feedback for the person in respect of the size and shape of the scotoma.

Further, training of the preferred retinal locus for fixation $P_p$ of the person can be carried out by means of the display unit 1 while the outer enveloping curve 13 is perceivable as a frame of the scotoma on the display unit 1 at all times by the person, as described above. By way of example, training of the preferred retinal locus for fixation $P_p$ is carried out with the goal of displacing the position of the preferred retinal locus for fixation $P_p$ to the first optimal preferred retinal locus for fixation $P_{v1}$ for the specific visual task v1. The outer enveloping curve 13 can be displayed on the display unit 1 here, in addition to a virtual reality or augmented reality scenario.

It was found that the combination of a virtual reality or augmented reality scenario with the display of the outer enveloping curve 13 as a frame of the scotoma makes the training of the preferred retinal locus for fixation $P_p$ particularly effective, in particular when using a head-mounted display as a display unit 1.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

1 Display unit
2 Fixation point
3 Sampling point
4 Polar axis
10 Visual field map
11 Polar sector
12 Outer boundary line
13 Outer enveloping curve
(ρ, θ) Polar coordinates
P Subjective visibility
F Fovea
Eye(x,y) Continuously captured eye alignment
$P_p$ Preferred retinal locus for fixation
v1 First specific visual task
v2 Second specific visual task
$P_{v1}$ First optimal preferred retinal locus for fixation
$P_{v2}$ Second optimal preferred retinal locus for fixation
($\rho_{Pv1}$, $\theta_{Pv1}$) First translation variables
($\rho_{Pv2}$, $\theta_{Pv2}$) Second translation variables

The invention claimed is:

1. A method for capturing a visual field of a person having a scotoma, the method comprising:
   continuously capturing an eye alignment of the person with a capturing unit;
   sampling a visual field of the person point-by-point to determine a plurality of points suitable for sight and a plurality of points not suitable for sight in a visual field of the person;
   finding the scotoma as a region with the plurality of the points not suitable for sight;
   calculating an outer boundary line of the scotoma;
   calculating an outer enveloping curve, which surrounds the outer boundary line of the scotoma at a predetermined distance; and
   displaying the outer enveloping curve on a display unit based on the continuously captured eye alignment, wherein the outer enveloping curve is perceivable as a frame of the scotoma by the person in case of alignment of an eye of the person onto the display unit,
   wherein the predetermined distance is an angular diameter of between 0.3° and 0.8°.

2. The method according to claim 1, further comprising:
   determining a position of a preferred retinal locus for fixation.

3. The method according to claim 1, further comprising:
   implementing the point-by-point sampling of the visual field of the person while the person fixates on a fixation point being permanently displayed on the display unit with a preferred retinal locus for fixation.

4. The method according to claim 3, further comprising:
   implementing the point-by-point sampling by intermittently displaying a sampling point on the display unit,
   wherein individual points of the visual field are successively captured in polar coordinates with a distance $\rho$ and an angle $\theta$ in respect of the preferred retinal locus for fixation during the point-by-point sampling with the sampling point.

5. The method according to claim 4, further comprising:
   capturing n points ($\rho$, $\theta$) by questioning the person in relation to a subjective visibility P of n points displayed on the display unit; and
   forming at least one of:
   a 3×n matrix with entries for ($\rho$, $\theta$, P) for the n captured points ($\rho$, $\theta$); or
   a visual field map as a graphical representation of the n captured points ($\rho$, $\theta$).

6. The method according to claim 3, further comprising:
   determining a fixation stability from the continuously captured eye alignment as a measure of a quality of the fixation by the preferred retinal locus for fixation on the fixation point displayed on the display unit.

7. The method according to claim 4, wherein a correction of the polar coordinates of a point ($\rho$, $\theta$) in the visual field is implemented by the continuously captured eye alignment should the fixation point at a moment of sampling the sampling point not be fixated by the preferred retinal locus for fixation.

8. The method according to claim 1, further comprising:
   recording an image of a fundus of the eye of the person;
   determining a position of a fovea from the image of the fundus of the eye; and
   storing at least one of the image of the fundus of the eye or the position of the fovea.

9. The method according to claim 2, further comprising:
   determining an optimal region for a specific visual task from points suitable for sight in the visual field of the person as a replacement for the preferred retinal locus for fixation.

10. The method according to claim 2, further comprising:
    storing current data of the person, wherein the stored current data includes a time of the respective determination for the eye or the eyes of the person, and at least one of the continuously captured eye alignment, the points suitable for sight in the visual field of the person, the points unsuitable for sight in the visual field of the person, the outer boundary line of the scotoma, the outer enveloping curve, the position of the preferred retinal locus for fixation, the position of the fovea, or the optimal region for a specific visual task as current data of the person, and
    producing a statement in relation to at least one of a further development of the scotoma of the person, the position of the preferred retinal locus for fixation of the person, or the optimal region of the person for a specific visual task from at least one of the current data of the person, from earlier correspondingly determined data of the person, or from correspondingly determined data of other persons.

11. The method according to claim 10, wherein the statements in relation to at least one of the further development of the scotoma of the person, the position of the preferred retinal locus for fixation of the person, or the optimal region of the person for a specific visual task are produced with artificial intelligence from the at least one of the current data of the person, from earlier correspondingly determined data of the person, or from correspondingly determined data of other persons.

12. The method according to claim 1, wherein the scotoma is a central scotoma.

13. An apparatus for capturing a visual field of a person having a scotoma, the apparatus comprising:
    a capturing unit for continuously capturing an eye alignment of the person,
    a display unit for displaying visual information, wherein the display unit is arranged with respect to a position of the eye of the person in at least one of a defined or a determinable spatial relationship, and
    a control unit for carrying out the method according to claim 1.

14. The apparatus according to claim 13, wherein the scotoma is a central scotoma.

15. The apparatus according to claim 13,
    wherein the display unit is a screen, and
    wherein the apparatus further comprises at least one of:
    means for placing a head of the person in a position that is defined relative to the screen; or
    means for determining a position of the head relative to the screen.

16. The apparatus according to claim 13, wherein the display unit is a spherically formed screen.

17. The apparatus according to claim 13, wherein the display unit and the capturing unit are provided in a head unit that is fastened to the head of the person.

18. A computer program stored on a non-transitory computer storage medium and having program code that is executable on a processor for carrying out the method according to claim 1.

19. A non-transitory computer storage medium having a computer program according to claim 18 stored thereon.

* * * * *

UNITED STATES PATENT AND TRADEMARK OFFICE
CERTIFICATE OF CORRECTION

PATENT NO. : 11,259,698 B2
APPLICATION NO. : 16/354424
DATED : March 1, 2022
INVENTOR(S) : Siegfried Wahl, Katharina Rifai and Maria Jose Barraza-Bernal It is certified that error appears in the above-identified patent and that said Letters Patent is hereby corrected as shown below:

In the Specification

In Column 12, Line 20, change "disappeares" to – disappears –

Signed and Sealed this
Seventeenth Day of May, 2022

Katherine Kelly Vidal
*Director of the United States Patent and Trademark Office*